United States Patent [19]
Koegel et al.

[11] Patent Number: 5,824,779
[45] Date of Patent: Oct. 20, 1998

[54] PHYTASE-PROTEIN-PIGMENTING CONCENTRATE DERIVED FROM GREEN PLANT JUICE

[75] Inventors: Richard G. Koegel, Madison; Richard J. Straub, Brooklyn; Sandra Austin-Phillips, Madison, all of Wis.

[73] Assignee: Wisconsin Alumni Research Foundation, Madison, Wis.

[21] Appl. No.: 638,448

[22] Filed: Apr. 26, 1996

[51] Int. Cl.$^6$ .............................. A61K 35/78; C07K 1/00; C12N 9/14; C07H 21/02
[52] U.S. Cl. ........................ 530/370; 530/350; 435/195; 435/410; 435/183; 435/430; 536/23.1
[58] Field of Search ..................................... 435/195, 410, 435/183, 430; 530/350, 370

[56] References Cited

U.S. PATENT DOCUMENTS

| | | |
|---|---|---|
| 2,600,903 | 6/1952 | Miller . |
| 3,297,548 | 1/1967 | Ware et al. . |
| 5,436,156 | 7/1995 | Van Gorcom et al. .............. 435/252.3 |
| 5,593,963 | 1/1997 | Van Ooijen et al. ..................... 514/12 |

OTHER PUBLICATIONS

Austin et al. (1994), *An overview of a feasibility study for the production of industrial enzymes in transgenic alfalfa*, Annals N.Y. Acad. of Sci., (721):234–242.
Austin et al. (1995), *Euphytica*, 00:1–13.
Ehrlich et al. (1993), *Biochem. & Biophys. Res. Comm.*, 195 (1): 53–57.
Gibson, D.M. and Ullah, A.B.J. (1990), *Inositol metabolism in plants*, Wiley–LISS, Inc., 77–82.
Han et al. (1995), Proceedings of the 1995 Cornell Nutrition Conference for Feed Manufacturers, Rochester, New York, pp. 149–152.
Hughes, G.P. and Eyles, D.E. (1952), *Extracted Herbage Leaf Protein for Poultry Feeding*, J. Agric. Sci (Cambridge), 43:136–143.
Knuckles et al. (1975), *Soluble protein from alfalfa juice by membrane filtration*, J. Agric. Food Chem., 2(22):209–212.
Knuckles and Kohler (1982), *Functional Properties of Edible Protein Concentrates From Alfalfa*, J. Agric. Food Chem., 30:748–752.
Koganov et al. (1988), *The Influence of Alternating Electric Current on Alfalfa Chloroplast Coagulation* (Original in russian), Phys. and Biochem. of Cultural Plants, 20(2):195–200.
Kohler et al. (1983), *LPC for Feed and Foods: The ProXan Process*, Telek and Graham, eds., "Leaf Protein Concentrates," AVI Publ. Co., pp. 508–524.
Ostrowski–Meissner, H.T. (1983), *Protein concentrates from pasture herbage and their fractionation into feed–and food–grade products*, Telek and Graham, eds., "Leaf Protein Concentrates," AVI Publ. Co., pp. 437–466.
Verwoerd et al. (1995), *Plant Physiology*, 109:1199–1205.

*Primary Examiner*—Lynette F. Smith
*Attorney, Agent, or Firm*—DeWitt Ross & Stevens SC

[57] ABSTRACT

A value-added composition of matter isolated from the juice of a transgenic green plant is disclosed. The composition of matter includes enzymatically-active phytase, xanthophylls, and dietary protein. The phytase is a gene product of an exogenous gene encoding for phytase which has been stably incorporated into the genome of the transgenic green plant, while the xanthophylls and the dietary protein are components native to the juice of the transgenic green plant.

8 Claims, 1 Drawing Sheet

PHYTASE-PROTEIN-PIGMENTING CONCENTRATE DERIVED FROM GREEN PLANT JUICE

FIELD OF THE INVENTION

The present invention is drawn to the production of industrially valuable enzymes and food grade protein from the juice of conventional or transgenic green plants. More specifically, the present invention is drawn to a multi-component, value-added composition of matter concentrated from the juice of transgenic green plants which contains phytase, dietary protein, and pigmenting compounds such as xanthophylls.

BIBLIOGRAPHY

Complete bibliographic citations of the references referred to herein can be found in the Bibliography section, immediately preceding the claims.

DESCRIPTION OF THE PRIOR ART

Green plants (the term "herbage" or "forage" is also used synonymously herein) are the most abundant source of dietary protein in the world. However, because green plant vegetation is generally too fibrous for direct human consumption, only low-fiber herbage or storage organs, such as fruits, seeds or tubers, are directly consumed by man. The remaining fibrous matter is normally used to feed ruminant animals whereby the plant protein is inefficiently converted into animal protein.

Mechanically, it is possible to separate harvested green plant material into a fibrous fraction and a juice fraction. Valuable protein concentrates, as well as other useful and economically valuable compounds, can then be isolated from the juice fraction. The remaining fibrous fraction may be utilized in a number of different ways, including as a high quality feed for ruminant animals or a source of lignocellulosic compounds.

The juice of green plants contains two major types of protein: particulate (or chloroplastic) protein and soluble (or cytoplastic) protein. The soluble protein is generally considered more valuable due to the versatility, functionality, and dietary significance of the proteins contained therein. For instance, the soluble protein fraction of green plant juice contains a wide variety of physiologically-significant enzymes.

It was hypothesized rather early in the development of large-scale commercial poultry production that the dietary requirements of egg-laying fowl might be met by utilizing protein-rich extracts from green plants. For instance, Hughes and Eyles (1953) describe a feeding trial with laying hens which used dietary protein extracted from the leaves of green plants. The authors hypothesized that dietary protein could be extracted from green plants in an economical fashion, thereby easing the shortage and lowering the cost of high protein feed in Great Britain.

However, in order to maximize the economic return of utilizing green plant protein fractions to the point of marketplace feasibility, it is necessary to maximize the amount of valuable soluble protein which can be recovered from the green plant material. For instance, it is known that both particulate and soluble protein can be precipitated together by heating the juice of green plants to about 80° C. Alternatively, the green particulate protein can be fractionated from the cream-colored soluble protein by heating green plant juice to 60° C. This will cause the green particulate protein fraction to precipitate from solution, where it can be separated by filtration or centrifugation. The soluble protein fraction can then be precipitated by raising the temperature of the juice solution to approximately 80° C.

Neither of these processes, however, maximizes the yield of the more valuable soluble protein fraction. Additionally, precipitation by thermal treatment irreversibly solidifies both the particulate protein and the soluble protein fractions. This greatly reduces the value and versatility of the proteins so isolated.

It is also well known to precipitate the particulate and soluble proteins from the juice of green plants by the addition of acid. Acidification results in the co-precipitation of an insoluble, green protein concentrate. While the concentrate has generally good nutritional properties, it lacks the functional versatility desired for food-grade modifiers. Also, its unappealing green color is a distinct aesthetic drawback.

It has been recognized by several researchers that if the soluble protein fraction, which accounts for approximately 40% of the total protein found in green plant juice, could be separated from the particulate protein, the soluble protein has economic potential as a versatile food additive. For instance, Knuckles and Kohler (1982) demonstrated that the soluble protein from alfalfa has desirable functional properties. From an economic viewpoint, Knuckles and Kohler estimated that as a food ingredient, the soluble protein from green plants would have a potential unit value 20–30 times higher than that of the crude, green protein concentrate. In short, even though soluble protein constitutes only about 2.5 to 3.5% by weight of the original dry mass of herbage, its increased value might have a significant impact on the economics of the wet fractionation process, described immediately below.

The process of wet fractionation, i.e., the physical maceration and expression of juice from the fibrous matrix of herbage, has been known for approximately two centuries. Using wet fractionation, approximately 20–30% of the most valuable dry matter (i.e., the various protein fractions), can be separated from the fibrous material of green plants. However, because alternative sources of protein have been, and continue to be, widely available, the positive economics of wet fractionation for the recovery of valuable protein products from herbage remains marginal to non-existent.

The advent of recombinant plant genetics has greatly spurred new investigations into the economics of manufacturing, isolating, and using exogenous proteins expressed in transgenic herbage plants such as alfalfa. In effect, valuable recombinant protein products, which are now produced by the fermentation of transgenic microorganisms, might be economically produced using transgenic plants rather than transgenic microbes.

Austin et. al. (1994) studied the production of industrial enzymes in transgenic alfalfa, a report of which appeared in the *Annals of the New York Academy of Sciences*. These investigators researched the feasibility of producing industrially important enzymes using alfalfa plants as "factories." Rather than using large-scale fermentation for the production of industrial enzymes, the focus of this study was whether, using genetic engineering technology, cloned genes for valuable enzymes could be expressed and economically harvested from heterologous plant hosts. The concept is economically attractive because many herbage plants are perennial, hardy crops, which are capable of more than one harvest per year. In the case of alfalfa specifically, in temperate climates such as those found in the midwestern United States, alfalfa does not require irrigation and is capable of three or more harvests a year. Moreover, since alfalfa is leguminous, it grows well without nitrogen fertilizer.

The Austin et al. paper noted above used a reporter gene, β-glucuronidase (GUS), as a model system. The analysis concluded that the concentration of the desired value-added product (in this case, GUS) in the resultant green plant juice is the most critical variable for economic viability. Analogous field studies for transgenic alfalfa which expresses α-amylase and manganese-dependent lignin peroxidase have also been reported by Austin et al. (1995).

An enzyme group of particular interest is the phytases. Phytases, more properly referred to as myo-inositol hexaphosphate phosphohydrolases, are a family of enzymes which catalyze the step-wise removal of inorganic orthophosphate from phytic acid (myo-inositol 1,2,3,4,5,6-hexakisphosphate). The economic interest in phytase is due to its ability to increase the bio-availability of inorganic phosphorous in phytate-containing non-ruminant animal feeds.

While phytase occurs widely in both plants and microorganisms, the enzyme has been extensively studied mostly from the filamentous fungi, particularly the Aspergilli, notably *A. ficuum*, and *A. nidulans*. For an excellent review of phytases and their action on phytic acid see Gibson, D. M. and Ullah, A. B. J. (1990), incorporated herein by reference.

Regarding the nucleotide sequences which encode phytase, several such sequences have been identified, sequenced, and cloned into various heterologous hosts. For instance, Van Gorcom et al., U.S. Pat. No. 5,436,156, incorporated herein by reference in its entirety, describe the isolation and cloning from *A. ficuum* of a DNA sequence coding for phytase. The isolated nucleotide sequence was successfully cloned and inserted into a vector capable of transforming a microbial expression host. Specifically, the nucleotide sequence was first cloned using the bacteriophage lambda AFD01, and further sub-cloned into pAN 8-1 and pUC19. The construct was then used to transform various types of filamentous fungi. (See also, EP 0 420 358 A1, to the same inventor.)

Ehrlich et al. (1993), describe the cloning and sequencing of a gene for a second type of phytase, designated PhyB. This phytase was isolated from *A. niger* NRRL 3135, and had a pH optimum of 2.5. PhyB was found to have different properties from the previously known phytase PhyA, which has a pH optimum of 5.0.

European Patent Application EP 0 449 375 A2 (Pen et al.) describes the expression of phytase from transgenic plants or plant organs. Here, the inventors describe DNA constructs which are capable of transforming plants with a gene which encodes for phytase, as well as the necessary regulatory sequences to enable the constitutive or tissue-specific expression of phytase. Using plasmid constructs, this EPO publication describes utilizing microbe-mediated transformation (e.g., via *Agrobacterium tumefaciens, A. rhizogenes*, and the like) to yield transgenic plants capable of expressing phytase. Depending upon the incorporation of the recombinant gene sequences into the plant genome, the phytase enzyme may be expressed in a stage-specific manner, as during fruit development, or the phytase may be expressed tissue-specifically, as in such plant organs as the fruit, tubers, leaves or seeds.

This reference is limited to a discussion of the end uses of the phytase produced by such transgenic plants. For instance, in addition to the use of phytase in feed additives for non-ruminants, the inventors note that phytase isolated from transgenic plants may be used in soy processing, or in the production in inositol from phytate. The inventors also note other uses in industries such as starch processing, fermentation, and brewing.

Verwoerd et al. (1995) describe the production and accumulation of phytase in the leaves of tobacco plants transformed with a phytase-coding gene of *A. niger*. This paper describes the constitutive expression of a phytase cDNA from transgenic tobacco plants. The exogenous phytase enzyme was secreted into the extracellular fluid at concentrations approximately 90 times higher than that in the total leaf extract. The phytase produced by the transgenic tobacco plants was compared to native Aspergillus phytase and found to have identical activities. This was despite the fact that the glycosylation of the tobacco phytase was different than that of the native Aspergillus phytase. During plant maturation, it was found that the phytase produced in the tobacco remained biologically active and accumulated in amounts up to 14.4% of the total soluble protein found in the tobacco.

As noted briefly, above, the economic interest in phytase is due to its ability to increase the bio-availability of inorganic phosphorous in phytate-containing non-ruminant animal feeds. The increase in intensive, large-scale livestock production has resulted in increased environmental problems, specifically eutrophication, due to the tremendous amount of manure produced in such enterprises. Phosphorous, an essential nutrient for both ruminants and non-ruminants, is often added to the feed provided to the livestock. Much of this feed material also contains large amounts of phytate. Phytate acts as the primary storage form of phosphorous in most green plant materials and can account for more than 50% of the total phosphorous content of the plant material. However, in monogastric animals, the phosphorous contained in phytate is poorly digested and largely excreted. Consequently, non-ruminant animal feeds are regularly supplemented with more easily assimilated forms of inorganic phosphorous. The excreted phytate, which contains large amounts of unutilized phosphorous, increases phosphorous loading to the environment, with concomitant environmental degradation.

Additionally, phytate is generally considered an anti-nutritional factor due to its ability to chelate multivalent cations. For instance, phytate will bind multivalent cations such as calcium, iron, manganese, and zinc, to form insoluble complexes. This reduces the bio-availability of these minerals, which is essential for proper growth and maturation. Further still, phytate also complexes with several different types of proteins, thereby obstructing enzymatic protein digestion.

As a consequence, several prior art references describe the use of phytase-containing compositions to increase the bio-availability of the phosphate contained in phytate.

For instance, European Patent Application EP 0 619 369 A1 (Vanderbeke et al.) describes a phytase-containing enzyme composition which remains enzymatically active at the low pH's found in the digestive tract of monogastric animals. This composition contains a combination of phytases and fungal acid phosphatases. The combination results in a synergistic effect which enables the mixture to enzymatically degrade phytate at relatively low pH. (See also, U.S. Pat. No. 5,443,979, to the same inventors.)

In a study reported in the Proceedings of the 1995 Cornell Nutrition Conference for Feed Manufacturers, in Rochester, N.Y., Han et al. reported that corn-soybean meal diets supplemented with microbial phytase significantly improved the utilization of phosphorous from such feeds and also decreased the amount of phosphorous excreted from swine by up to 50%. These researchers concluded that the need for inorganic phosphorous supplementation in swine feed stocks can be partially or totally eliminated by the addition of dietary microbial phytase during the growth and finishing phase of the swine. It should also be noted however, that the long term effects of phytase supplementation, if any, remain unknown.

Therefore, there remains a need for an affordable, renewable animal feed supplement which enables monogastric animals to more efficiently utilize inorganic phosphorous.

SUMMARY OF THE INVENTION

In light of the above discussion, the present invention is directed to a composition of matter concentrated from the juice of a transgenic green plant which expresses a functional exogenous gene product, the composition comprising the functional exogenous gene product, xanthophylls, and dietary protein.

The invention is directed to a composition of matter isolated or concentrated from the juice of a transgenic green plant which expresses exogenous phytase, the composition comprising enzymatically-active exogenous phytase, xanthophylls, and dietary protein.

The invention is further directed to a value-added composition of matter concentrated from the juice of a transgenic green plant comprising enzymatically-active phytase, xanthophylls, and dietary protein, wherein the phytase is a gene product of an exogenous gene encoding for phytase which has been stably incorporated into the genome of the transgenic green plant, and wherein the xanthophylls and the dietary protein are additional components of the juice of the transgenic green plant.

The present invention is also directed to a non-ruminant feed additive comprising dehydrated plant juice mechanically pressed from transgenic green plants which express enzymatically-active phytase.

The value-added multi-component concentrate of the present invention is particularly advantageous when added to non-ruminant animal feed. The multi-component concentrate allows non-ruminant animals to utilize phosphorous in the feedstuff more efficiently, thus greatly reducing or eliminating the need for phosphorous supplementation. In addition, use of the multi-component concentrate reduces phosphorous loading to the environment, thereby reducing environmental contamination.

Another notable advantage of the disclosed multi-component concentrate is its use in poultry feed. Because the concentrate contains high levels of pigments such as xanthophylls, and high levels of phytase, poultry feed which is supplemented with the multi-component concentrate need not be supplemented with phosphorous or pigmenting agents.

Another distinct advantage of the multi-component concentrate is that it is a value-added product as compared to the market value of the herbage matter from which it is prepared. This allows farmers and other agri-businesses to not only diversify their market offerings, but also to increase gross profit margins on otherwise fungible commodity goods.

The principal aim of the invention is to provide a value-added multi-component soluble protein concentrate from transgenic green plants which contains phytase, pigments such as xanthophylls, and dietary protein.

It is a further aim of the invention to provide a value-added multi-component protein concentrate from transgenic alfalfa which expresses exogenous phytase at high levels.

A still further aim of the present invention is to provide a supplement for monogastric feed rations which can be prepared directly from plant matter and which contains high levels of phytase, xanthophylls, and dietary protein.

Further aims, objects, and advantages of the above-described multi-component value-added concentrate will become apparent upon a complete reading of the Detailed Description, drawings, and attached claims, below.

BRIEF DESCRIPTION OF THE DRAWING

The sole drawing FIGURE depicts a flow chart describing the average yield of various products isolated from transgenic alfalfa which expresses phytase. The yields are listed on a per 1000 kilogram (kg) dry matter basis and, in parentheses, on a per acre expected annual yield basis.

DETAILED DESCRIPTION OF THE INVENTION

Transgenic Green Plants

An overriding motivation behind this invention is the use of common agricultural plants which have been genetically engineered to function as "enzyme factories." The use of common, albeit genetically engineered, plants in this fashion significantly impacts the economics of agricultural production. In the case of transgenic plants which express exogenous phytase, both the preferred plant starting material and the preferred exogenous gene product of the invention, the invention allows farmers to more effectively feed their non-ruminant livestock at greatly reduced prices, and also reduces phosphorous loading to the environment. Additionally, the multi-component composition is a value-added material which can be sold at a greater profit than the raw herbage matter itself.

Also of importance is that the multi-component composition described herein can be isolated from fresh herbage matter quite easily, at minimum expense in both time and equipment. This further improves the economics of exogenous protein production in agricultural green plants.

For the present invention, transgenic alfalfa is the preferred plant starting material. However, any suitably transformed plant species will function with comparable success. Included among the plant species which can be utilized in the present invention are cauliflowers, artichokes, apples, bananas, cherries, cucumbers, grapes, lemons, melons, nuts, oranges, peaches, pears, plums, strawberries, tomatoes, cabbages, endive, leeks, lettuce, spinach, tobacco, arrowroot, beets, carrots, cassava, turnips, radishes, yams, sweet potatoes, beans, peas, soya, wheat barley, corn, rice, rapeseed, millet, sunflower, oats, tubers, kohlrabi, potatoes, and the like. The plants are preferably common green field plants, such as alfalfa, tobacco, soya, corn, and the like, which have been engineered to express economically important enzymes in economically significant amounts. Transgenic alfalfa is most preferred because alfalfa is a hardy, perennial plant, which grows well with minimal fertilization and irrigation. Alfalfa is also a very prolific plant. In temperate areas such as those found in the Midwestern United States, alfalfa will yield three or more harvests per growing season.

Preferably, the plant starting material is stably transformed to express, constituitively or otherwise, enzymatically active phytase. However, a plant species stably transformed to express one or more gene products other than phytase may also be used. Phytase enzymes are produced in relatively large quantities by many microorganisms, most notably filamentous fungi of the genus Aspergillus. Phytase is also produced by bacteria such as *Bacillus subtilis*, yeasts such as *Saccharomyces cerevisiae*, and various strains of Pseudomonas. Among the filamentous fungi, *Aspergillus ficuum* (*A. ficuum*) produces a phytase which has a particularly high specific activity and thermostability. Phytase of high specific activity is also produced by *A. nidulans* and *A. niger*. In the present invention, it is preferred that the green plant starting material be transformed with one or more genetic elements which encode functional phytase, and that the genetic elements originate from a filamentous fungi selected from the group consisting of *A. ficuum, A. nidulans*, and *A. niger*.

The translocated genes may also include upstream or downstream regulatory elements, such as promoters for constitutive, growth stage-specific, or organ-specific expression, targeting sequences, secretory sequences, terminator sequences, polyadenylation signals, and the like, which might function to control gene expression in the heterologous host plant. Such regulatory elements may be homologous (native) to the host plant or they may be heterologous. All such regulatory sequences are known to those skilled in the art of recombinant genetics.

Means for producing stable transgenic plants is also well known in the art. Reference is made to European Patent Application 449 375 A2, published 2 Oct. 1991, for its teaching of the production of transgenic plants. The same is incorporated herein by reference in its entirety.

An illustrative method for producing transgenic plants, commonly referred to as the binary vector method, utilizes a strain of Agrobacterium containing a vir plasmid (which includes genes for virulence) and a second, compatible plasmid which contains the gene construct to be translocated.

Here, a double-stranded cDNA encoding phytase is prepared from mRNA isolated from a filamentous fungi of the genus Aspergillus, preferably *A. niger*. The DNA construct is linked with regulatory sequences from the gene encoding the 12S storage protein cruciferin from *Brassica napus*. The construct is then sub-cloned into a binary vector such as pMOG23 (*E. coli*. K-12 strain DH5α, Centraal Bureau voor Schimmelcultures, Baarn, The Netherlands, Accession No. CBS 102.90). The vector is then introduced into *Agrobacterium tumefaciens* containing a disarmed Ti plasmid. This can be done by any number of well known means, such as by electroporation. Bacterial cells containing the construct are co-cultivated with tissues from alfalfa or other plant to be transformed, and transformed plant cells are selected using nutrient media containing antibiotics. The transformed cells are induced to differentiate into plants on suitable nutrient media. The plants so produced will produce seeds which contain and express the gene construct.

To produce plants which constituitively express the phytase gene construct, the phytase-encoding gene construct is placed under the regulatory control of the 35S promotor sequence of the cauliflower mosaic virus (CMV). The construct is then subcloned into a binary vector as described above. The vector is then introduced into *Agrobacterium tumefaciens* containing a disarmed Ti plasmid. Bacterial cells containing the construct are co-cultivated with tissues from alfalfa or other plant to be transformed, and transformed plant cells are selected using nutrient media containing antibiotics. The transformed cells are induced to differentiate into plants on suitable nutrient media. The plants so produced constituitively express enzymatically active phytase.

Addressing each step more specifically, transgenic alfalfa which expresses phytase can be produced as follows:

Isolation of RNA from *Aspergillus sp.*: *A. ficuum* strain NRRL 3135 (or another desired Aspergillus species) is grown in a medium containing 22.72 g/l maize flour (amylase-treated at pH 7, 85° C. for 15 minutes), 9.36 g/l glucose, 2.9 g/l $KNO_3$, 0.142 g/l $MgSO_4 \cdot 7H_2O$ and 56.8 mg/l $FeSO_4 \cdot 7H_2O$. After 6 days the mycelium is harvested.

Dry mycelium (0.5 g) is frozen with liquid nitrogen and ground. The material is then thoroughly homogenized at 0° C. in 3M LiCl, 6M urea and maintained overnight at 4° C. Total cellular RNA is obtained by centrifugation at 16,000× g, followed by two successive extractions with a solution of phenol-chloroform-isoamylalcohol (50:48:2). The RNA is precipitated with ethanol and redissolved in 1 ml of 10 mM Tris-HCl (pH 7.4), 0.5% sodium dodecyl sulfate (SDS). For poly $A^+$ selection, the total RNA sample is heated for 5 minutes at 65° C., adjusted to 0.5M NaCl, and then applied to an oligo(dT)-cellulose column. After several washes with a solution containing 10 mM Tris, 1 mM EDTA, and 0.1 mM NaCl (pH 7.0), the poly $A^+$ RNA is collected by elution with 10 mM Tris (pH 7.0) and 1 mM EDTA.

Cloning cDNA Encoding Phytase: For the synthesis of the first strand of the cDNA, 5 μg of poly $A^+$ RNA, isolated as described above, is dissolved in 16.5 μl $H_2O$ and the following components are added: 2.5 μl RNasin (30 U/μl), 10 μl of a buffer containing 50 mM Tris-Hcl pH 7.6, 6 mM $MgCl_2$ and 40 mM KCl, 2 μl 1M KCl, 5 μl 0.1M DTT, 0.5 μl (oligo(dT)$_{12-18}$ (2.5 mg/ml), 5 μl 8 mM dNTP-mix, 5 μl BSA (1 mg/ml) and 2.5 μl Maloney MLV reverse transcriptase (200 U/μl). The mixture is incubated for 30 minutes at 37° C. and the reaction is stopped by addition of 10 μl 0.2M EDTA and 50 μl $H_2O$. An extraction is performed using 110 μl chloroform. After centrifugation for 5 minutes, 5M $NH_4Ac$ and 440 μl absolute ethanol (−20° C.) are added to the supernatant. Precipitation is done in a dry ice/ethanol solution for 30 minutes. After centrifugation (10 minutes at 0° C.), the cDNA/mRNA pellet is washed with 70% ice-cold ethanol. The pellet is dried and dissolved in 20 μl of $H_2O$.

Isolation of the cDNA encoding phytase is performed with the Polymerase Chain Reaction (PCR) in known fashion. Phytase from *A. ficuum* contains a BamHI site within the gene which allows the gene to be isolated in two fragments and then ligated at the BamHI site to create a full-length cDNA.

Partial sequencing of the phytase gene (Van Gorcom et al., U.S. Pat. No. 5,436,156, supra, incorporated by reference), reveals the presence of a BamHI site at approximately 800 base pairs from the initiation codon. The nucleotide sequence around this BamHI site, as well as the nucleotide sequence preceding the start codon and the nucleotide sequence after the stop codon of the phytase gene are used to design oligonucleotides for the PCR.

The polymerase chain reaction is performed according to the supplier of Taq-polymerase using 1.5 μl of the solution containing the reaction product of the first strand synthesis and 0.5 μg of each of the oligonucleotides. Amplification is performed in a PCR-licensed thermocycler. After 25 cycles of 2 minutes at 94° C., 2 minutes at 55° C., and 3 minutes at 72° C., the reaction mixture is deproteinized by subsequent phenol and chloroform extractions. The DNA is precipitated, redissolved in a buffer containing 10 mM Tris, pH 7 and 0.1 mM EDTA and subsequently digested with suitable restriction enzymes.

For the amplification of the fragment encoding the N-terminal part of the phytase protein, the two following oligonucleotides are used:

Oligo 1: 5' GGGTAGAATTCAAAAATGGGCGTCTCT-GCTGTTCTA 3' (SEQ. ID. NO: 1)

Oligo 2: 5' AGTGACGAATTCGTGCTGGTGGAGATG-GTGTCG 3' (SEQ. ID. NO: 2)

The amplified fragment is digested with EcoRI and cloned into the EcoRI site of pTZ18R (Pharmacia Biotech, Piscataway, N.J.). Restriction site mapping and nucleotide sequencing demonstrate the authenticity of the fragment. The resultant plasmid has been designated pGB925.

For amplification of the second fragment encoding the C-terminus of the phytase protein, the following two oligonucleotides are used:

Oligo 3: 5' GAGCACCAAGCTGAAGGATCC 3' (SEQ. ID. NO: 3)

Oligo 4: 5' AAACTGCAGGCGTTGAGTGTGATTGTT-TAAAGGG 3' (SEQ. ID. NO: 4)

The amplified fragment is digested with BamHI and Pstl and subsequently cloned into pTZ18R, which has been digested with BamHI and Pstl. Restriction site mapping and nucleotide sequencing show that the correct fragment is isolated. The resultant plasmid has been designated pGB926.

To isolate a full length cDNA, pGB925 is digested with EcoRI and BamHI and the fragment containing the phytase-encoding DNA is isolated. This fragment is cloned into plasmid pGB926, which has been digested with EcoRI and BamHI, resulting in plasmid pGB927. Plasmid pGB927 contains a full length cDNA encoding phytase.

The phytase gene from *Aspergillus ficuum* is tailored and cloned in an expression construct for constitutive expression in plants, downstream of the Cauliflower Mosaic Virus 35D promoter. The expression construct contains the coding information for a signal peptide sequence of plant origin. The entire construct is then introduced into a suitable binary vector (such as pMOG23, noted above). In pMOG23, the construct is inserted as an EcoRI/HindIII fragment into the binary vector pMOG23 which has been linearized with EcoRI and HindIII. The construct is then mobilized into *Agrobacterium tumefaciens* strain LBA4404 which contains a plasmid with the virulence genes necessary for T-DNA transfer to the plant. Transformation of alfalfa protoplasts then proceeds in standard fashion.

The above method is illustrative only, and several other genetic engineering techniques which result in stable transgenic plants will function with equal success in the present invention. As noted above, several such methods are well known in the genetic engineering art. The method by which the transgenic plant starting material is constructed is not critical for the performance of the present invention insofar as the resultant transgenic plants express a relatively large amount of functional exogeneous gene product.

Isolation of the Multi-Component Composition

Isolation of the multi-component composition according to the present invention preferably proceeds in four distinct steps. Throughout the four isolation steps, it is preferred that the temperature of the materials being handled does not exceed 45° C., and in no event exceeds 50° C. In the first step, the plant material is harvested, macerated, and the juice expressed therefrom. In the second step, the juice is gently heated, preferably by passing alternating current (AC) electricity through the juice. In the third step, aggregated particles within the juice are removed from the remaining soluble proteins. Lastly, the soluble protein fraction, which includes phytase, xanthophylls, and dietary protein, is concentrated by suitable means, such as ultrafiltration. Each of these steps will now be individually described in greater detail.

Juice Production

For the sake of brevity and clarity, the following shall be limited to a discussion of the isolation of a value-added, multi-component concentrate from transgenic alfalfa which expresses, constituitively or otherwise, phytase. This is for brevity and clarity only, and does not limit the invention disclosed herein in any fashion. A multi-component concentrate from the juice of other transgenic plant species which express other exogenous gene products can also be produced using the methodology described hereinbelow. The multi-component concentrate, containing phytase, pigments such as xanthophylls, and dietary protein can also be successfully obtained from the juice of any suitably-transformed plant which expresses increased levels of phytase.

Transgenic alfalfa which expresses phytase is the preferred plant species from which to isolate the multi-component composition of the present invention. The juice is preferably made from plant material in the late bud or early bloom stage. Expression of the juice from the plant material preferably occurs as soon as practicable after harvesting. It is preferred that juice expression take place within 24 hours after plant harvest. More preferable still is that juice expression take place within 1 hour after plant harvest.

For small batches of juice (up to approximately 15 liters), the alfalfa is first macerated in any suitable type of mechanical macerator, such as an impact macerator. The machine used in the initial studies included a 34 cm diameter rotor with four blunt blades which rotated in the horizontal plane at 3450 RPM. Alfalfa was impacted as it fell through the plane of the rotor.

The juice is then immediately expressed using any type of suitable means for pressing. For small batches, a hand-powered hydraulic basket press is perfectly suitable. For larger volumes of plant material, industrial-sized equipment is required. Any fiber or debris is removed by filtration. It is preferred that the juice be processed immediately after expression. The remaining fibrous material is an excellent feed for ruminant animals.

Treatment of Juice with Alternating Current

Koganov et al. (1988) report that direct exposure of alfalfa juice to alternating current (AC, 50 Hz) results in at least two benefits: first, the membranes on intact chloroplasts are disrupted allowing some soluble protein from within the chloroplasts to become part of the liquid; and second, the surface potential of the membranes are reduced from −260 mV for heat-coagulated material to −80 mV for the AC-treated material. This facilitates aggregation of non-soluble proteins. Further, while the reported process did not result in more total protein being recovered, it did yield a higher ratio of soluble protein to particulate protein.

For purposes of the present invention, an apparatus was designed and built to pass AC electricity directly through the plant juice. This AC electrical treatment is the prefered means of heating the juice because it gently and evenly heats the juice, without generating localized hot spots which might result in enzyme inactivation. The preferred treatment protocol is a modification of the protocol described by Koganov et al., above.

An initial apparatus in the form of a flow-through chamber with two walls defining fixed electrodes was built. This first apparatus proved unsuccessful because of the juice velocity profile. The velocity of the juice actually in contact with the electrodes in the flow-through chamber was too slow. This caused the juice adjacent to the electrodes to overheat, causing the protein within the juice to coagulate and adhere to the electrodes. This reduces the conductivity of the electrodes to almost zero.

To overcome this problem, electrodes in the form of spinning disks were mounted in a trough or flume through which the juice was passed. In this manner, it is possible to vary juice throughput rate, electrode voltage, and electrode RPM accurately and reproducibly. Juice output temperature is continuously monitored to guard against overheating. At all times during the electrical treatment, the temperature of the juice does not exceed 50° C. It is greatly preferred that the temperature of the juice never exceed 45° C. Generally, a current of approximately 2.5 amps/cm$^2$ (16 amps/in$^2$) of electrode area satisfies these requirements.

It is preferred that the juice be treated in this fashion, and maintained at a temperature of approximately 35° C., for a short duration (30 minutes to 2 hours, 1 hour preferred) to facilitate aggregation of the particulate protein in the juice.

The AC treatment described herein differs from the Koganov treatment in that the rotating stainless steel electrodes are immersed directly in the alfalfa juice. The electrodes in Koganov's apparatus were immersed in a salt (NaCl) solution which was separated from the alfalfa juice by bipolar membranes. The membranes were interposed to eliminate any possible contamination of the juice by the electrode material.

Separation of Particulate Protein and Soluble Protein Concentration

Ultrafiltration as a means of concentrating the protein within fresh, whole juice has not generally been considered practical due to the blinding of the filters caused by the particulate materials (Amundson (1992), Ostrowski-Meissner, (1983).) Ultrafiltration has, however, been successfully used to concentrate protein from juice which had previously been clarified by removal of particulate protein after heat coagulation at 55°–60° C. (See, for instance, Knuckles et al. (1975), also incorporated herein by reference in its entirety.)

In the present invention, it is preferred that the plant juice first be clarified by centrifugation (10,000×g) prior to protein concentration to remove aggregated particulate proteins. The remaining soluble protein then is concentrated 5 to 10-fold, preferably by ultrafiltration.

Romicon or Millipore (Marlborough, Mass.) filters with nominal 10,000 molecular weight cut-off limit function quite satisfactorily. Batch sizes in various test runs ranged from a few liters to 200 liters. For larger batches a filter area of 4.6 m$^2$ (50 ft$^2$) is preferred, for small batches a filter area of 0.2 m$^2$ (2 ft$^2$) is preferred. Pressure drops of approximately 175 kPa (25 psi) should be maintained through the filters. In any event, the instructions supplied by the filter manufacturer should be followed.

Protein Measurement

Measurement of the relative amounts of protein in the juice or juice fractions can be ascertained by coagulation of proteinaceous materials at 80° C. (176° F.). After the protein materials have been coagulated, they can be separated from any remaining liquids by filtration through paper of the kind used in coffee making. After filtration, the coagulum is rinsed to minimize the presence of dissolved solids in the adhering liquid. When drainage is complete, a pre-tared filter paper and the coagulum are oven-dried at 103° C. (217° F.) for 24 hours to determine the dry matter in the coagulum. Since the resultant coagulum is not 100% protein, its dry matter weight can only be used as a measure of the relative concentration of protein between two different treatments or in the liquid before and after a given treatment.

Kohler et al. (1983) report the protein concentration in the coagulum obtained from whole alfalfa juice at 60° C. (140° F.) and from clarified alfalfa juice at 80° C. (176° F.) as 45% and 90% respectively. The former is largely chloroplastic protein with associated particulate material while the latter is largely soluble (cytoplasmic) protein.

Alternative Processing Pathways

In addition to the preferred separation and concentration techniques described above, several other techniques can also be employed with equal success. Among these techniques are:

1) high voltage electrostatic concentration;
2) low voltage DC concentration;
3) freeze-thaw aggregation;
4) flocculents; and
5) vacuum drum filtration.

As noted above, however, the preferred protocol from both a technical and an economic standpoint proceeds in the four steps described above.

Target enzyme(s), such as heterologous phytase, may be purified from this concentrate, or, preferably, the concentrate is used per se as a non-ruminant animal feed supplement containing phytase, pigments such as xanthophylls, and dietary protein.

EXAMPLE

Figure 1:
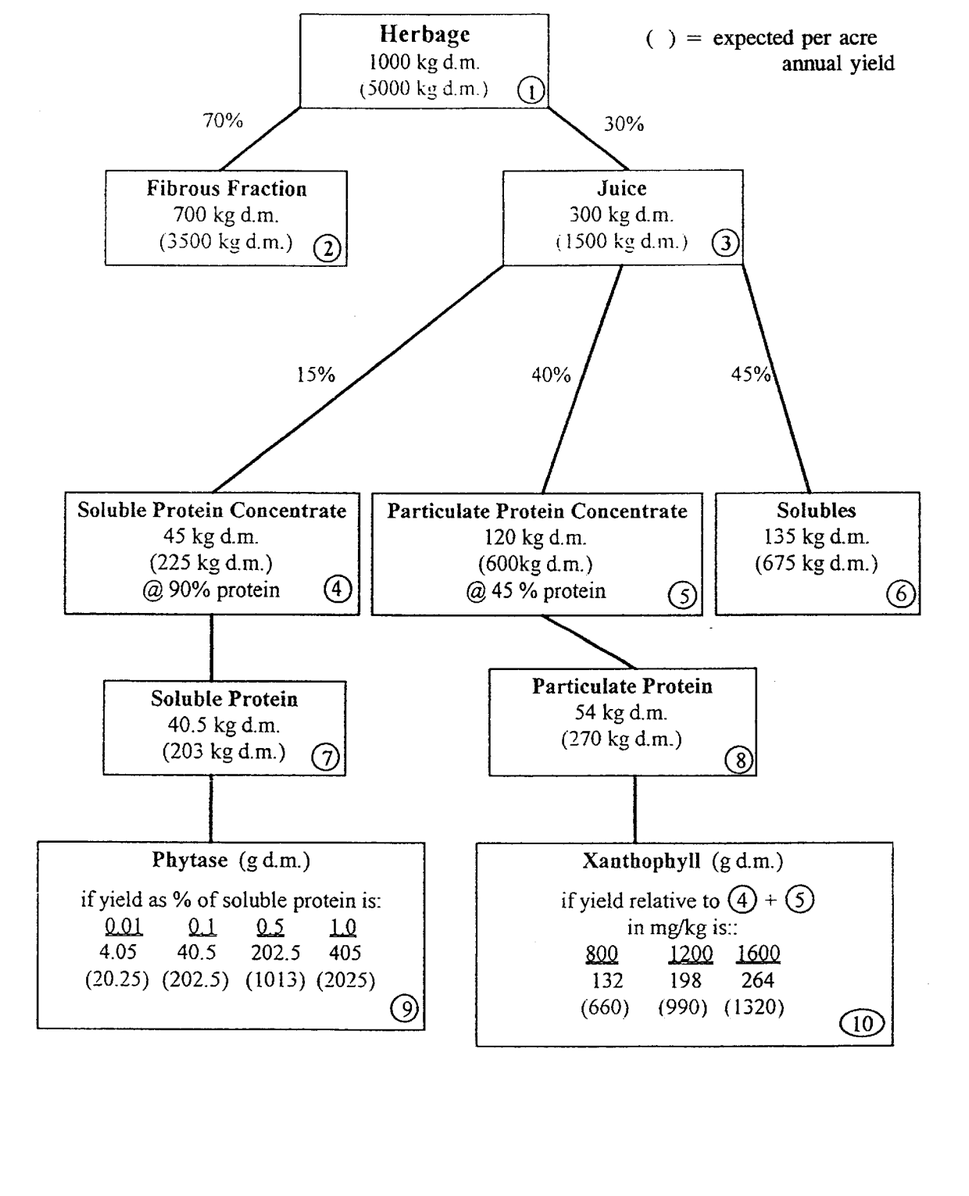

In order to more fully illustrate the present invention, the following Example is provided. The Example, which makes reference to the sole drawing FIGURE, is for illustration purposes only to aid in a complete understanding of the invention. The Example does not limit the scope invention disclosed and claimed herein in any fashion.

Expected Yields

This Example reports the expected yields of various alfalfa juice fractions, including phytase and xanthophylls, isolatable from transgenic alfalfa which constituitively expresses exogenous phytase originating from A. niger. Freshly expressed alfalfa juice was analyzed no less than 140 times on 40 days spanning a single growing season in Dane County, Wis., extending from mid-June to mid-October. The results are tabulated in the sole drawing FIGURE.

Each box of the FIGURE includes two designations. The first designation is the amount of the respective fraction based upon 1000 kg of harvested dry matter. The second designation is the amount of the respective fraction based upon an expected per acre annual yield. This designation is placed in parentheses ( ). The Example tabulates the complete isolation of soluble and particulate protein, phytase, and xanthophylls. In its use as a dietary supplement, the multi-component composition of matter stops short of the complete isolation of the individual components of the composition as this is not necessary to exploit the advantages of the transgenic alfalfa. This Example is solely to illustrate the relative amounts of soluble protein, particulate protein, phytase and xanthophylls which can be recovered from transgenic alfalfa.

As shown in boxes 2 and 3 of the FIGURE, each 1000 kg of dry matter (d.m.) after expression of the juice contained therein yields on average 700 kg of fibrous matter and 300 kg of juice, respectively. The fibrous matter can be used for any number of purposes, including as a feed for ruminants.

As depicted in box 4, the soluble protein fraction makes up approximately 15% by weight of the juice, 90% of which is, on average, protein. Particulate proteins make up approximately 40% by weight of the juice (box 5), and 45% by weight of the juice is made up of other soluble components such as salts, sugars and the like (box 6).

Referring now to box 7, approximately 40.5 kg of soluble protein can be isolated per 1000 kg of dry herbage. Box 9 tabulates the amount of phytase which is, on average, contained within the soluble protein fraction as a function of the percent phytase present in the soluble protein fraction. For instance, if the soluble protein fraction contains 0.01 weight percent phytase, approximately 4.05 grams of phytase, on average, can be isolated from 1000 kg of dry herbage. If the soluble protein fraction contains 1.00 weight percent phytase, approximately 405 grams of phytase, on average, can be isolated from 1000 kg of dry herbage.

Boxes 9 and 10 detail the amount of particulate protein and xanthophylls which are found, on average, in alfalfa juice, respectively. As noted in box 10, the amount of xanthophylls present in the multi-component composition is calculated as a function of the ration of the amount of soluble protein versus the amount of particulate protein isolated from the juice. The amount of xanthophylls recovered is directly proportional to the sum of soluble proteins plus particulate proteins. Consequently, as the amount of total protein increases, so does the amount of xanthophylls recovered.

Non-Ruminant Feed Supplement

Using the above average yields, the following conclusions can be drawn regarding the ability to supplement non-ruminant animal feeds with the multi-component supplement described above.

First, regarding phytase activity and the requirements of poultry and swine, the following requirements are generally accepted in the animal nutrition art:

1 unit phytase=1 $\mu$mole $PO_4$ released/min @ pH 5.15 and 37° C.

Pure phytase=100 to 140 units per mg dry matter

Poultry require 300 to 500 units phytase per kg ration, which corresponds to approximately 3.33 mg phytase per kg of ration, or 3.33 g phytase per metric ton of ration.

Swine require approximately 1000 to 1200 units phytase per kg ration, which corresponds to approximately 9.16 mg phytase per kg of ration, or 9.16 g phytase per metric ton of ration.

For this Example, poultry were considered to require 29 mg xanthophyll per kg ration, or 29 g xanthophyll per metric ton ration. Swine do not require xanthophyll.

The ratio of xanthophyll to phytase in poultry rations should preferably approximate a ration of 8.6:1 xanthophyll to phytase. This ratio is approximated when the xanthophyll yield is about 1,000 mg/kg of boxes 4 and 5 of the FIGURE (i.e. the fraction of soluble vs. particulate proteins isolated from the juice), and phytase is produced at the rate of approximately 0.05% of the soluble protein fraction (box 7 of the FIGURE).

At these rates, one acre of transgenic alfalfa produces enough phytase to supplement 30.4 metric tons of poultry feed. At a higher phytase yield of 0.5% phytase in the soluble protein fraction, the per acre yield of phytase is sufficient to supplement 304 metric tons of poultry feed.

Since swine rations require approximately 2.5 times the amount of phytase as compared to poultry rations, one acre of transgenic alfalfa yielding 0.5% phytase in the soluble protein fraction produces sufficient phytase to supplement 120 metric tons of swine ration.

It should also be noted that since swine do not require xanthophylls, there is economic potential to remove the xanthophylls present in the multi-component composition by means of solvent extraction in the event that the composition is destined for swine feed.

It is understood that the invention is not confined to the particular construction and arrangement of parts herein illustrated and described, but embraces such modified forms thereof as come within the scope of the following claims.

BIBLIOGRAPHY

Austin et al. (1994), An overview of a feasibility study for the production of industrial enzymes in transgenic alfalfa, Annals N.Y. Acad. of Sci., (721):234–242.

Austin et al. (1995), *Euphytica*, 00:1–13.

Ehrlich et al. (1993), *Biochem. & Biophys. Res. Comm.*, 195(1): 53–57.

Gibson, D. M. and Ullah, A. B. J. (1990), *Inositol metabolism in plants*, Wiley-LISS, Inc., 77–82.

Han et al. (1995), Proceedings of the 1995 Cornell Nutrition Conference for Feed Manufacturers, Rochester, N.Y., pp. 149–152.

Hughes, G. P. and Eyles, D. E. (1952), *Extracted Herbage Leaf Protein for Poultry Feeding*, J. Agric. Sci (Cambridge), 43:136–143.

Knuckles et al. (1975), *Soluble protein from alfalfa juice by membrane filtration*, J. Agric. Food Chem., 23(2):209–212.

Knuckles and Kohler (1982), *Functional Properties of Edible Protein Concentrates From Alfalfa*, J. Agric. Food Chem., 30:748–752.

Koganov et al. (1988), *The Influence of Alternating Electric Current on Alfalfa Chloroplast Coagulation* (Original in russian), Phys. and Biochem. of Cultural Plants, 20(2): 195–200.

Kohler et al. (1983), *LPC for Feed and Foods: The ProXan Process*, Telek and Graham, eds., "Leaf Protein Concentrates," AVI Publ. Co., pp. 508–24.

Ostrowski-Meissner, H. T. (1983), Protein concentrates from pasture herbage and their fractionation into feed- and food-grade products, Telek and Graham, eds., "Leaf Protein Concentrates," AVI Publ. Co., pp. 437–66.

Verwoerd et al. (1995), *Plant Physiology*, 109:1199–1205.

---

What is claimed is:

1. A non-ruminant feed additive consisting essentially of dehydrated plant juice from transgenic alfalfa which express enzymatically-active transgenic phytase.

2. The non-ruminant feed additive according to claim 1, further consisting of xanthophylls and dietary protein, wherein the xanthophylls and the dietary protein are native components of the juice of the transgenic alfalfa.

3. The non-ruminant feed additive according to claim 1, wherein the transgenic phytase is a gene product of an Aspergillus gene encoding phytase.

4. The non-ruminant feed additive according to claim 3, wherein the transgenic phytase is a gene product encoded by one or more genes selected from the group consisting of *A. ficuum* phytase genes, *A. nidulans* phytase genes, and *A. niger* phytase genes.

5. The non-ruminant feed additive according to claim 4, wherein the transgenic phytase is a gene product of an *A. niger* phytase gene.

6. A method of feeding a non-ruminant animal comprising:

(a) transforming alfalfa constituitively to express exogenous, enzymatically active phytase; and then (b) mechanically pressing juice from the transformed alfalfa of step (a) to yield alfalfa juice containing the expressed phytase; and then (c) feeding the juice of step (b) to a non-ruminant animal.

7. The method of claim 6, wherein in step (a), the alfalfa is transformed to express a phytase selected from the group consisting of *A. ficuum* phytase, *A. nidulans* phytase, and *A. niger* phytase.

8. The method of claim 7, wherein in step (a), the alfalfa is transformed to express *A. niger* phytase.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

-continued (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GGGTAGAATT CAAAAATGGG CGTCTCTGCT GTTCTA     36

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

AGTGACGAAT TCGTGCTGGT GGAGATGGTG TCG     33

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GAGCACCAAG CTGAAGGATC C     21

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

AAACTGCAGG CGTTGAGTGT GATTGTTTAA AGGG     34